(12) United States Patent
Sun et al.

(10) Patent No.: US 9,636,435 B2
(45) Date of Patent: May 2, 2017

(54) METHOD FOR SHAPING TISSUE MATRICES

(75) Inventors: Wendell Sun, Warrington, PA (US); Gary Monteiro, Branchburg, NJ (US)

(73) Assignee: LifeCell Corporation, Branchburg, NJ (US)

( * ) Notice: Subject to any disclaimer, the term of this patent is extended or adjusted under 35 U.S.C. 154(b) by 228 days.

(21) Appl. No.: 13/177,720

(22) Filed: Jul. 7, 2011

(65) Prior Publication Data

US 2012/0010728 A1 Jan. 12, 2012

Related U.S. Application Data

(60) Provisional application No. 61/362,424, filed on Jul. 8, 2010.

(51) Int. Cl.
*A61L 27/36* (2006.01)
*A61L 27/50* (2006.01)

(52) U.S. Cl.
CPC .......... *A61L 27/3604* (2013.01); *A61L 27/50* (2013.01)

(58) Field of Classification Search
None
See application file for complete search history.

(56) References Cited

U.S. PATENT DOCUMENTS

| | | | |
|---|---|---|---|
| 4,865,602 A * | 9/1989 | Smestad et al. | 623/23.56 |
| 5,336,616 A | 8/1994 | Livesey et al. | |
| 5,364,756 A | 11/1994 | Livesey et al. | |
| 5,397,353 A * | 3/1995 | Oliver et al. | 600/36 |
| 5,772,439 A | 6/1998 | Yamaoka et al. | |
| 6,706,684 B1 * | 3/2004 | Bayon et al. | 514/17.2 |
| 6,734,018 B2 | 5/2004 | Wolfinbarger, Jr. et al. | |
| 2003/0035843 A1 | 2/2003 | Livesey et al. | |
| 2003/0143207 A1 | 7/2003 | Livesey et al. | |
| 2003/0229394 A1 * | 12/2003 | Ogle et al. | 623/2.14 |
| 2006/0073592 A1 | 4/2006 | Sun et al. | |
| 2007/0248575 A1 | 10/2007 | Connor et al. | |
| 2008/0027542 A1 | 1/2008 | McQuillan et al. | |
| 2008/0131473 A1 * | 6/2008 | Brown et al. | 424/423 |
| 2009/0035289 A1 | 2/2009 | Wagner et al. | |
| 2009/0306790 A1 | 12/2009 | Sun | |
| 2010/0161054 A1 | 6/2010 | Park et al. | |
| 2011/0002996 A1 | 1/2011 | McQuillan et al. | |
| 2011/0022171 A1 | 1/2011 | Richter et al. | |

FOREIGN PATENT DOCUMENTS

| | | | |
|---|---|---|---|
| FR | 2 786 400 | | 6/2000 |
| GB | 1073243 | * | 6/1963 |
| GB | 1 073 243 | | 6/1967 |
| GB | 1073243 | * | 6/1967 |
| WO | WO 2005/009134 | | 2/2005 |
| WO | WO 2009/049568 | | 4/2009 |

OTHER PUBLICATIONS

Bourroul et al., "Sterilization of Skin Allografts by Ionizing Radiation," *Cellular and Molecular Biology* 48(7):803-807 (2002).
Brockbank et al., "Vitrification: Preservation of Cellular Implants," Ch. 12, Topics in Tissue Engineering, pp. 1-26 (2003).
European Search Report for PCT/US2005/036433 mailed Oct. 10, 2007, from the European Patent Office.
Ghosh et al., "A Comparison of Methodologies for the Preparation of Human Epidermal-Dermal Composites," *Ann. Plastic Surgery* 39(4):390-404 (1997).
Huang et al., "Use of periacetic acid to sterilize human donor skin for production of acellular dermal matrices for clinical use," *Wound Repair and Regeneration* 12(3):276-287 (2004).
International Search Report and Written Opinion for PCT/US2005/36433 mailed Aug. 30, 2006, from the International Searching Authority of the United States Patent and Trademark Patent Office.
International Search Report and Written Opinion for PCT/US2011/043129 mailed Oct. 17, 2011, from the International Searching Authority of the European Patent Office.
Yoshinaga et al. "Protection by Trehalose of DNA from Radiation Damage," *Biosci. Biotech. Biochem.* 61(1):160-161 (1997).

* cited by examiner

*Primary Examiner* — Maury Audet
(74) *Attorney, Agent, or Firm* — McCarter & English, LLP; Matthew R. Van Eman

(57) ABSTRACT

Methods for shaping tissue matrices are provided. The methods can be used to produce shaped tissue products that retain desired biologic properties without using chemical crosslinking agents.

14 Claims, 14 Drawing Sheets

METHOD FOR SHAPING TISSUE MATRICES

This application claims priority under 35 U.S.C. §119 to U.S. Provisional Patent Application 61/362,424, which was filed on Jul. 8, 2010.

The present disclosure relates to tissue matrices, and more particularly, to methods for shaping tissue matrices and tissue products produced according to those methods.

Various tissue-derived products are used to regenerate, repair, or otherwise treat diseased or damaged tissues and organs. Such products can include intact tissue grafts and/or acellular or reconstituted acellular tissues (e.g., acellular tissue matrices from skin, intestine, or other tissues, with or without cell seeding). However, such tissues generally have a shape defined by their tissue of origin. For example, dermal or intestinal products will generally include sheets of relatively flexible materials.

To treat certain tissue or organ defects, it may be desirable to form predefined shapes or configurations that more closely conform to anatomic structures to be treated. Accordingly, methods for altering the shape of tissue matrices, as well as tissue matrices produced using those methods, are provided.

SUMMARY

According to certain embodiments, a method for shaping a tissue matrix is provided. The method comprises selecting a collagen-containing tissue matrix; partially dehydrating the tissue matrix; applying mechanical forces to the tissue matrix to change the orientation of collagen fibers within the tissue matrix; and exposing the tissue matrix to radiation.

In certain embodiments, a tissue product is provided. The product comprises an extracellular tissue matrix comprising collagen, wherein the extracellular tissue matrix has a three-dimensional shape formed by a process comprising partially dehydrating the extracellular tissue matrix; applying mechanical forces to the tissue matrix to reorient collagen fibers within the tissue matrix; and exposing the tissue matrix to radiation.

In certain embodiments, a tissue product is provided. The product comprises an extracellular tissue matrix comprising collagen fibers, wherein at least some of the collagen fibers within the matrix have an orientation that is different than the orientation of the fibers in a tissue from which the matrix is produced and the matrix forms a stable three dimensional shape, and wherein the matrix has a denaturation temperature as measured with differential scanning calorimetry that is within 5° C. of the denaturation temperature of the tissue from which the matrix is produced.

In certain embodiments, a tissue product is provided. The product comprises an extracellular tissue matrix comprising collagen fibers, wherein at least some of the collagen fibers within the matrix have an orientation that is different than the orientation of the fibers in a tissue from which the matrix is produced, and wherein the matrix forms a stable three-dimensional shape without using chemical cross-linking agents.

DESCRIPTION OF CERTAIN EXEMPLARY EMBODIMENTS

Figure 1:
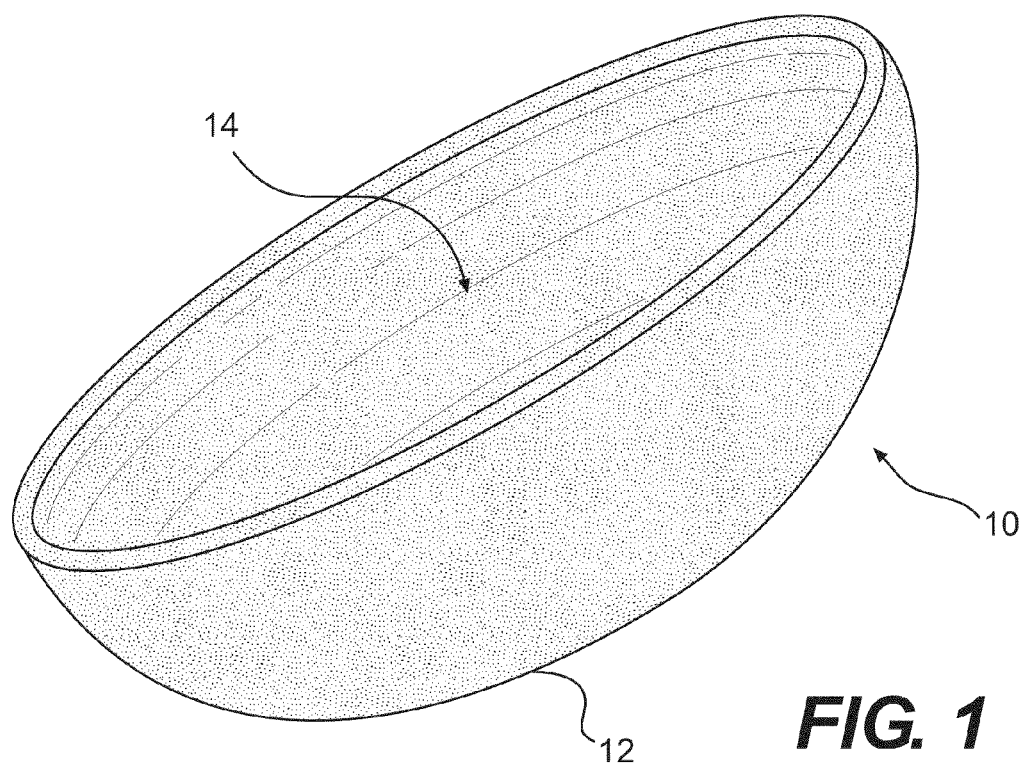
FIG. 1 is a shaped tissue product, according to certain embodiments.

Reference will now be made in detail to certain exemplary embodiments according to the present disclosure, certain examples of which are illustrated in the accompanying drawings. Wherever possible, the same reference numbers will be used throughout the drawings to refer to the same or like parts.

In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Any range described herein will be understood to include the endpoints and all values between the endpoints.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

As used herein "tissue product" and "shaped tissue product" will refer to any human or animal tissue that contains an extracellular matrix and that has been processed to change the orientation of at least some of the collagen fibers within the extracellular matrix. "Tissue products" can include acellular or partially decellularized tissue matrices, decellularized tissue matrices that have been repopulated with exogenous cells, and/or cellular tissues that have been processed to change the orientation of at least some of the collagen fibers within the tissue's extracellular matrix.

Various human and animal tissues can be used to produce products for treating patients. For example, various tissue products for regeneration, repair, augmentation, reinforcement, and/or treatment of human tissues that have been damaged or lost due to various diseases and/or structural damage (e.g., from trauma, surgery, atrophy, and/or long-term wear and degeneration) have been produced. Such products can include, for example, acellular tissue matrices, tissue allografts or xenografts, and/or reconstituted tissues (i.e., at least partially decellularized tissues that have been seeded with cells to produce viable materials).

In certain embodiments, these products can be completely or partially decellularized to yield acellular tissue matrices or extracellular tissue materials to be used for patients. For example, various tissues, such as skin, intestine, bone, cartilage, nerve tissue (e.g., nerve fibers or dura), tendons, ligaments, or other tissues can be completely or partially decellularized to produce tissue products useful for patients. In some cases, these decellularized products can be used without addition of exogenous cellular materials (e.g., stem cells). In certain cases, these decellularized products can be seeded with cells from autologous sources or other sources to facilitate treatment. Suitable processes for producing acellular tissue matrices are described below.

Tissue products can be selected to provide a variety of different biological and mechanical properties. For example, an acellular tissue matrix or other tissue product can be selected to allow tissue ingrowth and remodeling to assist in regeneration of tissue normally found at the site where the matrix is implanted. For example, an acellular tissue matrix, when implanted on or into fascia, may be selected to allow regeneration of the fascia without excessive fibrosis or scar formation. In certain embodiments, the tissue product can be formed from ALLODERM® or STRATTICE™, which are human and porcine acellular dermal matrices respectively. Alternatively, other suitable acellular tissue matrices can be used, as described further below. The methods for shaping tissues having an extracellular matrix can be used to process any collagenous tissue type, and for any tissue matrix product. For example, a number of biological scaffold materials are described by Badylak et al., and the methods of the present disclosure can be used to produce tissues with a stable three-dimensional shape using any of those materials, or any other similar materials. Badylak et al., "Extracellular Matrix as a Biological Scaffold Material: Structure and Function," *Acta Biomaterialia* (2008), doi: 10.1016/j.actbio.2008.09.013.

Most tissues, when first harvested from an animal or cadaver donor, retain the general shape of the original tissue source. For example, a skin graft, when first dissected from a donor, will generally form a flat, flexible sheet when placed on a flat surface. Similarly, urinary bladder, small intestine, blood vessels, dura, and other materials will retain the shape of the original tissue source. Further, when cut and processed (e.g., to produce an acellular tissue matrix) most tissues can be laid on a flat surface to form a relatively flat sheet.

For some applications, it may be desirable to alter the shape of tissue products. For example, acellular tissue matrices are implanted at a variety of different anatomic sites, and it may be beneficial to control the shape of the tissue matrices to more closely conform to the desired shape when implanted. For example, acellular tissue matrices or other tissue products can be implanted around breast implants; around or replacing vascular structures; around or replacing luminal structures (e.g., ureters, nerves, lymphatic tissues, gastrointestinal structures); on or replacing heart valves, pericardium, or other cardiac structures; in or on bony or cartilaginous materials (e.g., ears, noses, articular surfaces, around dental structures, or along any short of long bone); and/or surrounding, lining, supporting, or replacing any body cavity (e.g., bladder, stomach). However, some processes that may alter the shape of a tissue product to form a stable three-dimensional structure can also alter the tissue matrix in undesirable ways. For example, chemical cross-linking can be used to form a stable three-dimensional structure, but excessive cross-linking can alter the biologic properties of the tissue, and chemical cross-linking agents may be harmful to patients when implanted in a patient. Accordingly, methods for controlling the shape of tissue products are provided.

According to certain embodiments, a method for shaping a tissue matrix is provided. The method comprises selecting a collagen-containing tissue matrix; partially dehydrating the tissue matrix; applying mechanical forces to the tissue matrix to change the orientation of collagen fibers within the tissue matrix; and exposing the tissue matrix to radiation. In certain embodiments, a tissue product is provided. The product comprises an extracellular tissue matrix comprising collagen, wherein the extracellular tissue matrix has a three-dimensional shape formed by a process comprising partially dehydrating the extracellular tissue matrix; applying mechanical forces to the tissue matrix to reorient collagen fibers within the tissue matrix; and exposing the tissue matrix to radiation. In certain embodiments, a tissue product is provided, which comprises an extracellular tissue matrix comprising collagen fibers, wherein the extracellular tissue matrix forms a stable three-dimensional shape that is different than a three-dimensional shape of a tissue from which the matrix is produced, and wherein the matrix has a denaturation temperature, as measured with differential scanning calorimetry, is within 5° C. of the denaturation temperature of the tissue from which the matrix is produced. In certain embodiments, a tissue product is provided. The product comprises an extracellular tissue matrix comprising collagen fibers, wherein at least some of the collagen fibers within the matrix have an orientation that is different than the orientation of the fibers in a tissue from which the matrix is produced, and wherein the matrix forms a stable three-dimensional shape without using chemical cross-linking agents.

Figure 2:
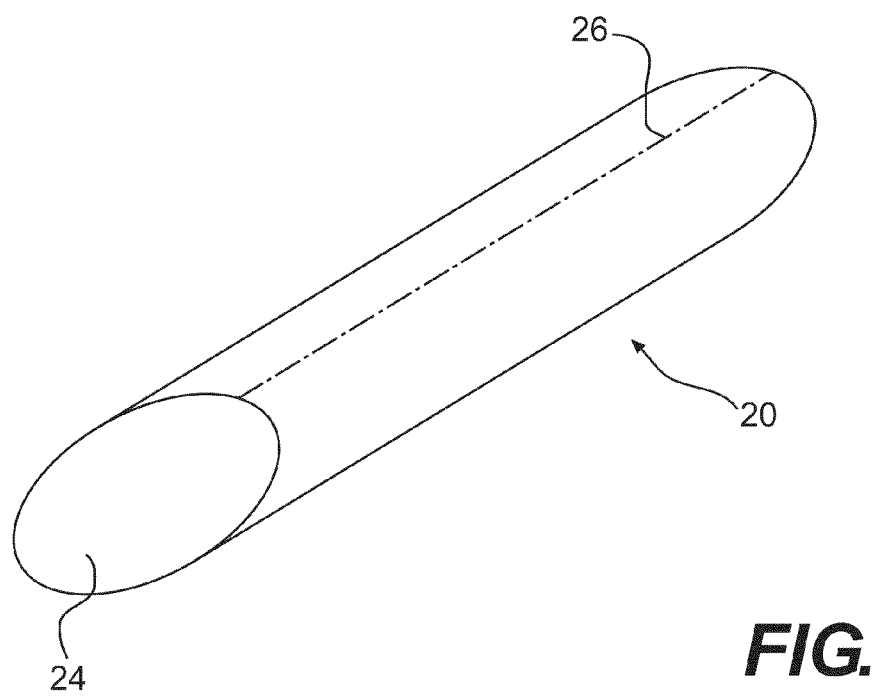
FIG. 2 is a shaped tissue product, according to certain embodiments.
Figure 3:
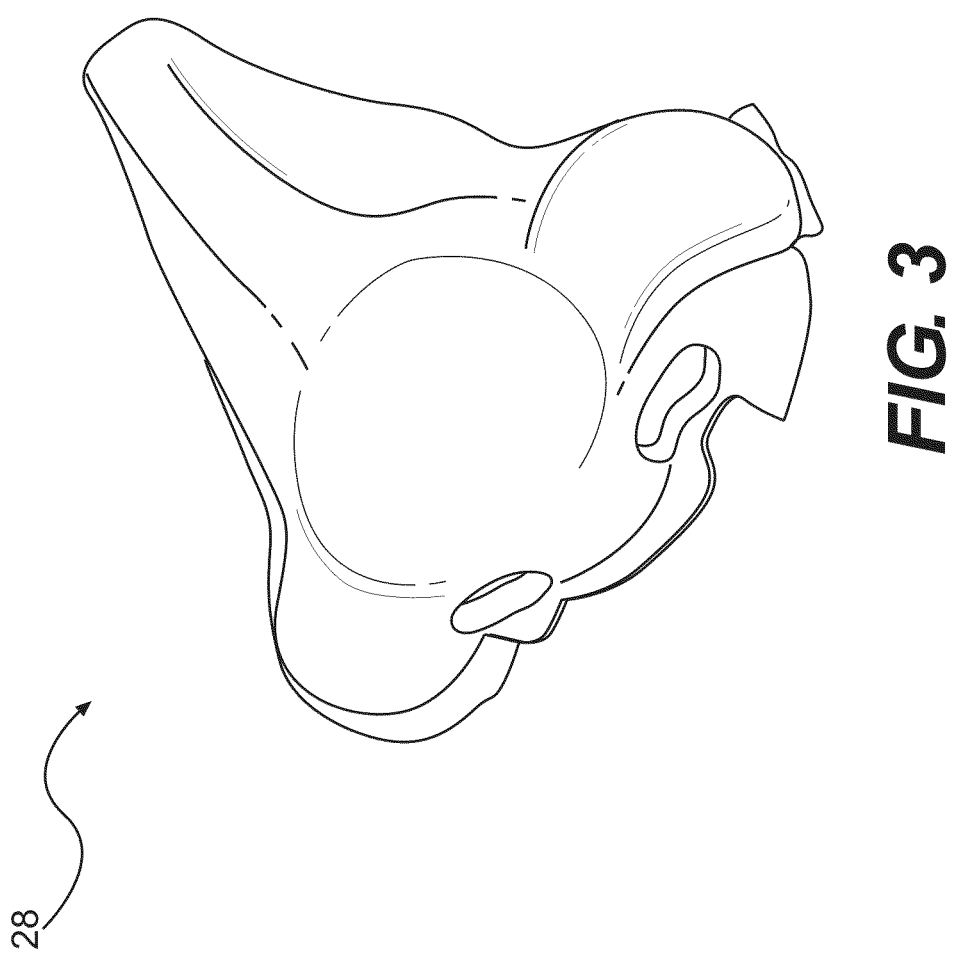
FIG. 3 is a shaped tissue product, according to certain embodiments.

As noted above, the tissue products of the present disclosure comprise an extracellular matrix that has a stable three-dimensional shape. The three-dimensional shape can be selected to conform to any anatomic structure and/or to perform any desired structural or functional task in or on a patient's body. For example, FIGS. 1-3 are shaped tissue products, according to certain embodiments. FIG. 1 is a cup-shaped device 10, having a convex back surface 12 and a concave inner surface 14. Cup-shaped devices may be useful to support breast implants, e.g., for breast augmentation and/or reconstruction. For example, the inner surface 14 may be placed around a breast implant and attached to surrounding fascia, muscle, or other tissue to help secure a breast implant in a proper position, to reduce or prevent scar formation, or to otherwise alter the aesthetic appearance of an implant. In addition, such devices by be used to reinforce body cavities (e.g., bladder or stomach).

Such devices can be modified, e.g., made oblong, completely spherical, and/or more convex or concave, as the need may be. Further, the shape can be made as a custom-shaped product, e.g., to conform to specific anatomic or aesthetic requirements, or can be a standard size for a particular application (e.g., to conform to standard implants, such as a breast implant, used in conjunction with the shaped tissue products).

FIG. 2 is a tubular device 20 having a lumen 24. If formed from a sheet of tissue, the device 20 may include a seam 26 that is held together with sutures, adhesive, or other connection mechanisms. Tubular devices may be useful for treatment of conditions related to bodily luminal structures and/or for treatment of connective tissue structures. For example, a tubular structure may be useful for treating, replacing, or reinforcing vascular structures (e.g., arteries or veins), as a conduit to assist in nerve repair or regeneration, and/or to replace, repair, or regenerated tendons, ligaments, or fascia. The methods of the present disclosure can be used to produce three-dimensional shapes for any anatomic structure. FIG. 3 is a nose-shaped tissue product 28 that was produced from an acellular dermal matrix using methods of the present disclosure. Products having shapes conforming to any desired anatomic structure can be produced using the methods described herein.

The collagen-containing tissue matrix can include an acellular tissue matrix or a tissue matrix that forms part of an intact or partially decellularized tissue. In some embodiments, the tissue matrix comprises a dermal tissue matrix. In certain embodiments, the tissue is selected from fascia, pericardial tissue, dura, umbilical cord tissue, placental tissue, cardiac valve tissue, ligament tissue, tendon tissue, arterial tissue, venous tissue, neural connective tissue, urinary bladder tissue, ureter tissue, and intestinal tissue.

As noted, the process of shaping tissue products includes partially dehydrating tissues. It has been discovered that partial dehydration of tissues causes the extracellular matrix of collagenous materials to become more pliable, thereby allowing collagen fibers to be reoriented. However, excessive dehydration, e.g., by freeze-drying, can make tissues brittle, and therefore, excessive dehydration can damage tissues during subsequent processing steps.

A variety of suitable processes can be used to partially dehydrate the tissue matrix. For example, suitable methods can include blot-drying with water-absorbent towels, isothermal water desorption with controlled humidity, applying mechanical forces to tissues, centrifugation, and/or controlled and/or directional freezing. Any suitable method can be used to partially dehydrate the matrix as long as the method does not cause undesirable tissue alterations.

In various embodiments, the amount of dehydration is selected based on the tissue type to be processed and the desired shapes to be produced. In some embodiments, the tissue is dehydrated to produce a tissue matrix containing between 95% (w/w) and 50% (w/w) water content. In other embodiments, the tissue product is dehydrated to produce a water content that is between 80% (w/w) and 65% (w/w).

After partial dehydration, mechanical forces are applied to tissues or acellular tissue matrices to reorient collagen fibers within the extracellular matrix of the tissues. This can be done in a variety of ways, as long as forces are directed in such a way to produce a final desired shape. In some embodiments, a mold having a desired shape is produced, and a sheet of tissue or acellular tissue matrix, which has been partially dehydrated, is placed in contact with the mold. Forces are then applied to portions of the sheet to reorient fibers to produce a tissue product having a shape corresponding to the mold. For example, in some embodiments, to produce a cup-shaped product, as shown in FIG. 1, a mold having a convex surface is used, and a sheet is stretched or pulled over the mold and held in place with sutures. Similarly, to produce a tubular product, as shown in FIG. 2, a dowel rod or other tubular structure is selected as a mold, and a sheet of tissue or acellular tissue matrix is wrapped around the sheet.

The amount, direction, and/or manner of applying force may depend in the shape that is desired. For example, for a relatively simple shape, it may be sufficient to simply lay a sheet of acellular tissue over a mold having the desired shape, and additional force may be applied to stretch of compress the matrix. In other cases, for example, to produce a more complex shape, a sheet of acellular tissue matrix can be placed on a mold, and a second mold having a corresponding configuration can be placed on top of the acellular tissue matrix to compress the matrix and form a desired shape.

For example, as described above, FIG. 3 illustrates another shaped tissue product 28, according to certain embodiments. Product 28 has a nose shape, and may be used as a tissue graft to repair or reshape nasal structures. Product 28 was produced by placing an acellular dermal matrix between two shaped molds, to produce the desired shape, and irradiating the matrix in the shaped configuration.

After collagen fibers are reoriented, tissue products are treated to stabilize the three-dimensional structures of the extracellular matrix. In some embodiments, the structure is stabilized by exposing the tissue product to radiation. Radiation may cause a small degree of tissue cross-linking sufficient to produce a stable three-dimensional structure. The stable structure will tend to conform to a shape similar to the mold (or shape of the matrix at the time of irradiation), but will be sufficiently flexible to allow the tissue product to be manipulated during surgery and to function as a soft-tissue graft. For example, a tissue product shaped as a cup for a breast implant, will be flexible enough to conform to a breast implant and not produce undersirable texture, while maintaining a relatively cup-shaped configuration in a resting state. Similarly, a tubular product for a vascular device will be sufficiently flexible to allow bending, anastomosis with a vascular site, and expansion under vascular pressure, but will maintain a tubular shape when in a resting state (i.e., when no external mechanical forces are placed on it).

In various embodiments, the amount of radiation to which the product is exposed can be between 5 Gy and 50 kGy, or between 5 Gy and 20 kGy. In certain embodiments, the radiation is applied at a dose of less than 10 kGy, less than 5 kGy, or less than 1 kGy. Suitable forms of radiation can include gamma radiation, e-beam radiation, and X-ray radiation.

As noted above, the tissue products of the present disclosure can form a stable three-dimensional structure without causing undesirable alterations in the tissue matrix. For example, although cross-linking may assist in maintaining a three-dimensional shape, excessive crosslinking can alter the biological properties of tissue products. Therefore, in some embodiments, the tissue product will maintain a three-dimensional structure without excessive crosslinking.

Tissue cross linking can be measured by an increase in a denaturation temperatures of a tissue matrix, as measured with differential scanning calorimetry. Accordingly, in some embodiments, tissue products of the present disclosure include an extracellular tissue matrix that forms a stable three-dimensional shape that is different than a three-dimensional shape of a tissue from which the matrix is produced, and wherein the matrix has a denaturation temperature on a differential scanning calorimetry thermogram that is within 5° C. of the denaturation temperature of the tissue from which the matrix is produced. In certain embodiments, the denaturation temperature as measured with differential scanning calorimetry is within 3° C., within 2° C., or within 1° C. of the denaturation temperature of the tissue from which the matrix is produced. In various embodiment, the denaturation temperature can be at a peak on the DSC curve, or be identified as an average from the denaturation onset to end temperature, so long as the same method is used to identify the denaturation temperature in the source and processed tissues. Further, since chemical crosslinking agents can cause non-uniform and excessive crosslinking and/or may be harmful, the method of the present disclosure allows formation of a matrix that has a stable three-dimensional shape without using chemical cross-linking agents.

As noted above, "shaped tissue products," can include acellular or partially decellularized tissue matrices, decellularized tissue matrices that have been repopulated with exogenous cells, and/or cellular tissues that have been processed to change the orientation of at least some of the collagen fibers within the tissue's extracellular matrix. Accordingly, in various embodiments, tissue products may be processed (e.g., to remove cellular components to produce acellular tissue matrices, and/or to remove antigenic materials), using steps other than those needed to shape the tissue product. In various embodiments, the methods for shaping tissue products can be performed before and/or after other processing steps. For example, for an acellular tissue matrix product, the shaping can be performed after the decellularization process or on the intact tissue, which is then processed to remove cells. Further, in some embodiments, since radiation is used to stabilize the three-dimensional shape, the irradiation step may be performed as part of a terminal sterilization step to both stabilize the tissue product shape and destroy pathogens. In other embodiments, radiation is applied to the tissue product to produce a stable three-dimensional shape, and the tissue is sterilized using subsequent radiation steps and/or other sterilization processes.

In addition, tissue products shaped according to the methods of the present disclosure may be packaged and/or rehydrated. In certain embodiments, the products can be stabilized with low-dose radiation then rehydrated and packaged. Subsequent to packaging, the products may be terminally sterilized with additional radiation or using other sterilization processes.

In certain embodiments, tissue products produced according to methods of the present disclosure have a permeability that is different than the permeability of tissue matrices from which they are made. In various embodiments, the permeability can be to liquids, including aqueous liquids, such as blood, serosanguinous fluids, urine, or other bodily fluids.

In certain embodiments, the shaped tissue products will have a reduced permeability to liquids than the matrices from which they are produced. Tissue products having a reduced permeability may be more suitable for treating anatomic sites exposed to large amounts of fluids, or which should retain or exclude fluids to perform normal functions. For example, when repairing, replacing, or regenerating portions of vascular or urinary structures, it may be desirable to have a reduced (or little to no) permeability, thereby preventing leakage of floods such as blood or urine while cellular ingrowth and tissue regeneration occurs. Therefore, in certain embodiments, shaped tissue products can include tubular structures that are substantially impermeable to blood or pouch like structures that are impermeable to blood, urine, or other fluids.

Experiment #1

Reorientation of Collagen Fibers in Acellular Human Dermis

Processing of Tissue to Decellularize and Reorient Collagen Fibers:

Human skin from cadaver donors was obtained, and the upper portion was split to a thickness of about 2 mm. The donor skin was de-epidermized for 17 hours at room temperature by incubation in a 1.0 M sodium chloride solution containing 0.5% (w/v) TRITON X100. The tissue was de-cellularized by incubation for 22 hours in 2% (w/v) sodium deoxycholate. The de-epidermized and de-cellularized tissue matrix was washed in Dulbecco's phosphate-buffered saline (PBS, pH 7.5) containing 5 mM ethylenediaminetetraacetic acid (EDTA), and was frozen at −80° C. for temporary storage. Frozen dermis was thawed at room temperature (~22° C.) and rinsed with Dulbecco's PBS solution overnight.

The tissue matrix was partially dehydrated by blot-drying with sterile GAMMA WIPES® to achieve tissue matrix hydration of 3.12±0.22 g water per gram dry mass (mean±standard deviation, N=3) or a final water content of 75.7% (w/w). The partial dehydration represented the removal of ~51% of the water in the tissue matrix. The blotting process was also used to apply mechanical pressure (compression) to the partially dehydrated tissue matrix to cause reorientation of collagen fibers within the tissue matrix.

Dehydrated and reoriented tissue matrix samples were sealed in sterile plastic film bags. The plastic film bags were then sealed in secondary foil-to-foil bags and were irradiated with 500 Gy gamma radiation over 35 minutes. After radiation, the tissue matrix was rehydrated in PBS. The water content of the rehydrated tissue matrices were 4.92±0.31 gram water per gram of dry tissue mass (N=3) or 83.1°)/0 (w/w), representing a 57.7% increase during rehydration in PBS. The rehydrated human tissue matrices had an estimated porosity of about 88±1% (N=3).

Figure 4:
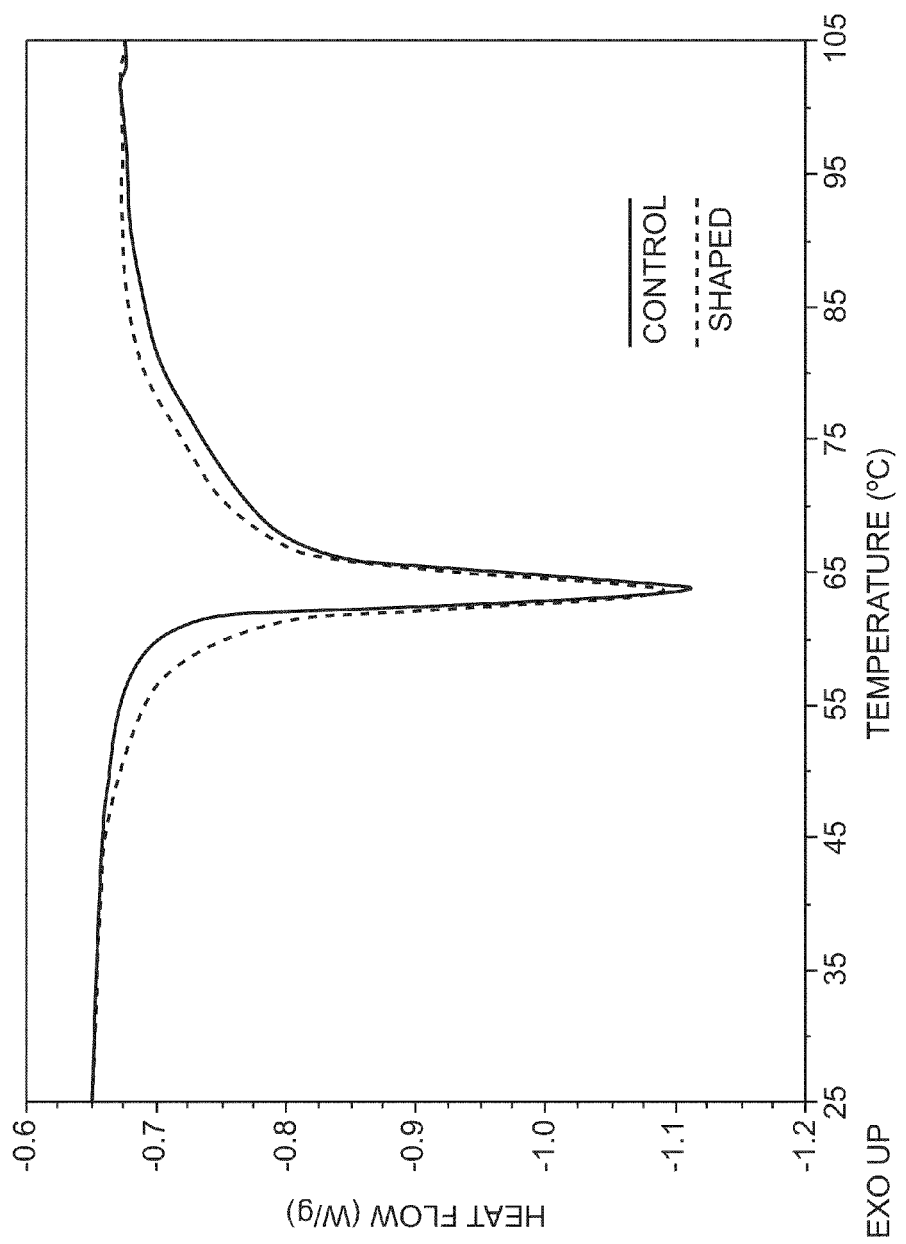
FIG. 4 is a differential scanning calorimetry thermogram for an acellular human dermal material and a shaped tissue product produced according to certain embodiments.

Differential Scanning Calorimetry:

Differential scanning calorimetry (DSC) was used to assess the differences between control tissue matrices (decellularized but not subjected to collagen reorientation) and rehydrated shaped tissue product. FIG. 4 is a differential scanning calorimetry thermogram for a control acellular human dermal material and a shaped tissue product. As shown, the thermograms for the control material and the shaped tissue product were very similar, having a similar denaturation temperature indicating little collagen crosslinking or damage. Therefore, the collagen fiber reorientation with partial dehydration and low dose gamma radiation did not significantly alter the structure and stability of the collagen fibers and the tissue matrix.

Electron Microscopy:

Rehydrated tissue matrices were fixed in 2% glutaraldehyde for 24 hours and dehydrated sequentially in 25%, 50%, 75%, 90%, 98% and 100% (v/v) ethanol solutions. The duration of each ethanol dehydration step was at least 2 hours. Ethanol-dehydrated samples were dried in hexamethyldisilazane and were then sputter-coated with gold before scanning electron microscope (SEM) observation under 10 kilovolts.

Figure 5A:
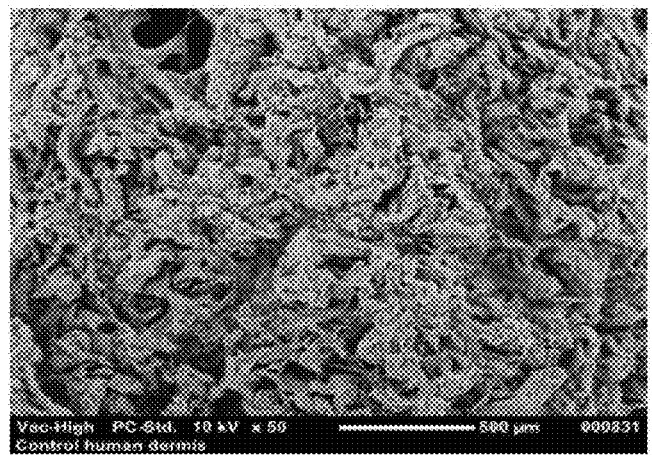
FIGS. 5A-5D are scanning electron micrographs for an acellular human dermal material and a shaped tissue product produced according to certain embodiments.
Figure 5B:
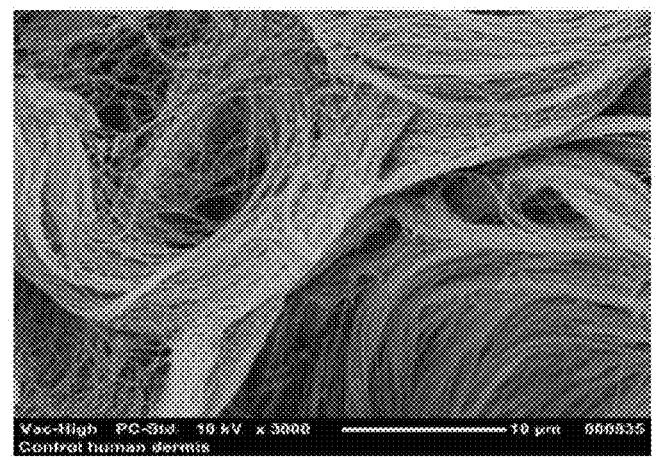
Figure 5C:
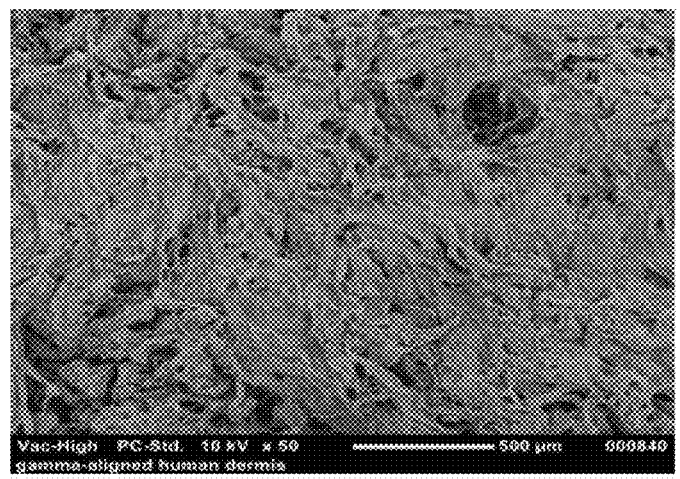
Figure 5D:
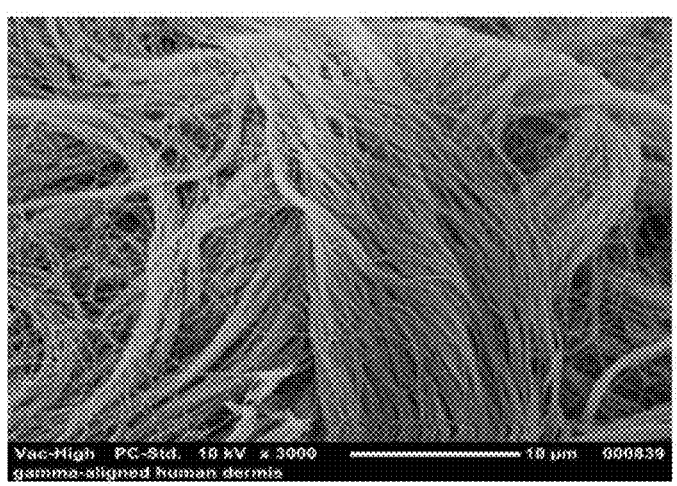

FIGS. 5A-5D are scanning electron micrographs for control acellular human dermal material (FIGS. 5A and 5B) and a shaped tissue product (FIGS. 5C and 5D). The low magnification images (FIGS. 5A and 5C) show that the treatment resulted in collagen fiber realignment. Further, the higher magnification images (FIGS. 5B and 5D) demonstrate that the processing did not alter the collagen fiber structures.

Experiment #2

Reorientation of Collagen Fibers in Acellular Porcine Dermis

Processing of Tissue to Decellularize and Reorient Collagen Fibers:

Porcine skin was split to remove the epidermis and subcutaneous fat. The remaining tissue was 1.9±0.2 mm thick (N=5). The tissue was de-cellularized by incubation in 2% (w/v) sodium deoxycholate for 24 hours at room temperature, and was then washed three times with PBS for 2 hours each wash. The de-cellularized dermal matrix was partially dehydrated by blot-drying with sterile GAMMA WIPES® to achieve a tissue hydration level of 2.34±0.37 gram water per gram of dry tissue mass or a final water content of 70% (w/w). The dehydration removed ~43% tissue water. The blotting process was also used to applied mechanical pressure (compression) to the tissue matrix to cause reorientation of collagen fibers within the tissue matrix.

Tissue samples were sealed in sterile plastic film bags. The plastic bags were sealed in secondary foil-to-foil bags and were irradiated with 500 Gy gamma-irradiation over 35 min. After gamma irradiation, porcine dermal matrix was rehydrated in PBS. The fully rehydrated tissue matrix had a hydration of 2.84±0.38 gram water per gram dry tissue mass (N=10) or a water content of 74% (w/w). The rehydrated porcine dermis matrix had an estimated porosity about 80±2% (N=10) according to the water content in tissue matrix.

Figure 6:
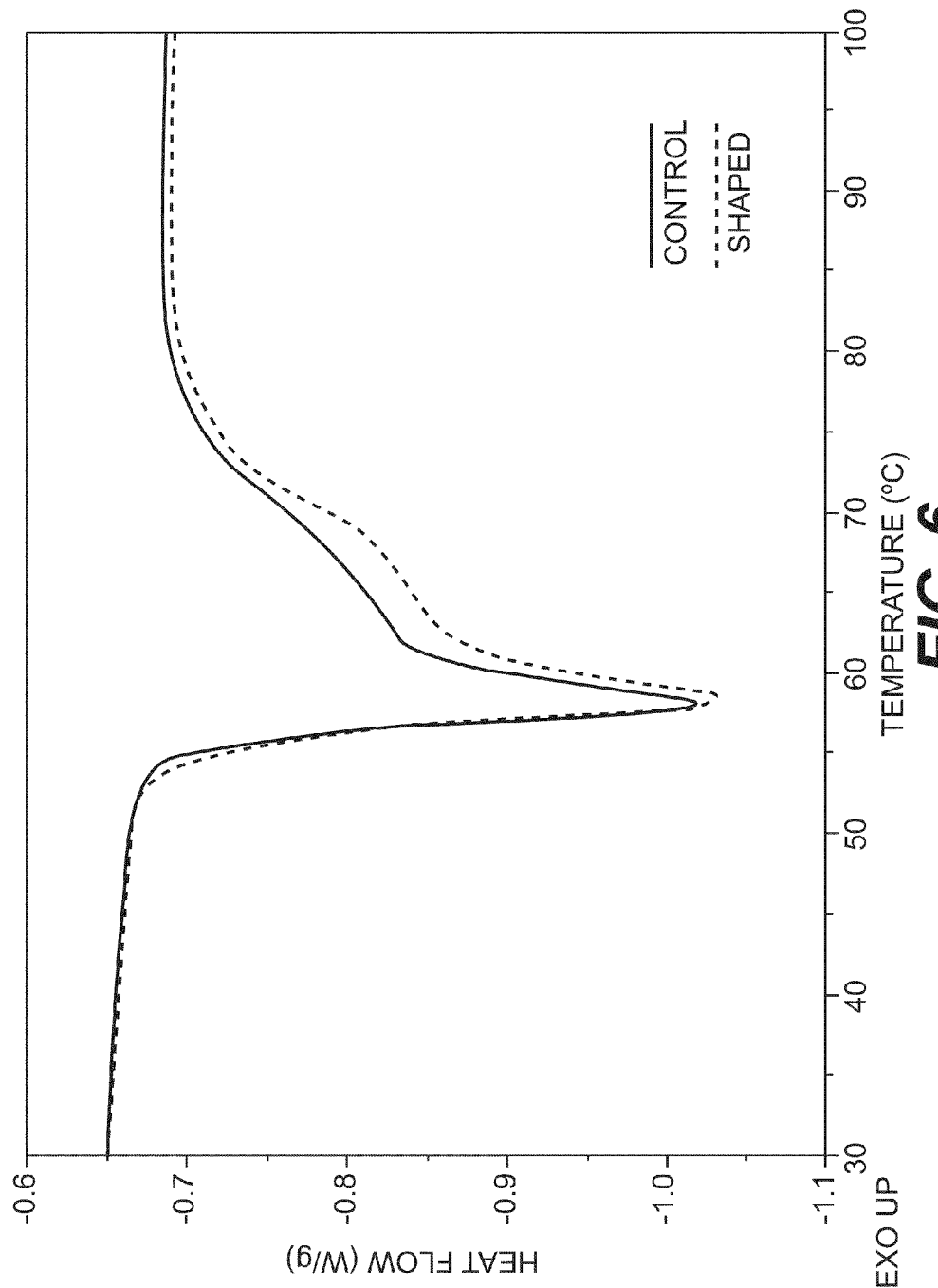
FIG. 6 is a differential scanning calorimetry thermogram for an acellular porcine dermal material and a shaped tissue product produced according to certain embodiments.

Differential Scanning Calorimetry:

Differential scanning calorimetry (DSC) was used to assess differences between control tissue matrices (decellularized but not subjected to collagen reorientation) and the rehydrated shaped tissue product. FIG. 6 is a differential scanning calorimetry thermogram for a control acellular porcine dermal material and a shaped tissue product. As shown, the thermograms for the control material and the shaped tissue product were similar, as the shaped tissue product had a denaturation temperature on the thermogram that was shifted to a slightly to higher temperature (1 to 2° C.). The small shift caused by collagen reorientation and gamma irradiation was indicative of a small amount of collagen crosslinking.

Figure 7A:
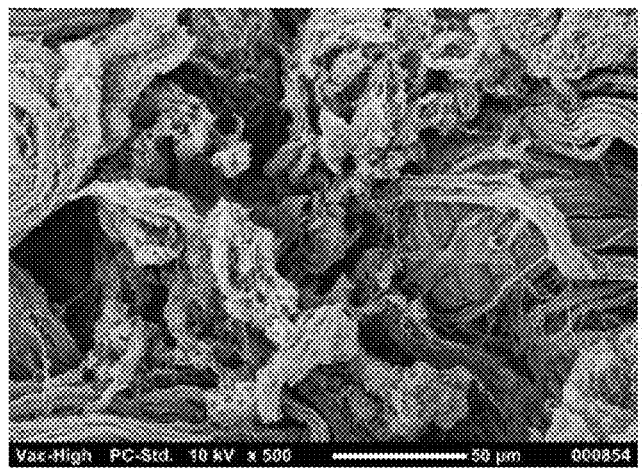
FIGS. 7A-7D are scanning electron micrographs for an acellular porcine dermal material and a shaped tissue product produced according to certain embodiments.
Figure 7B:
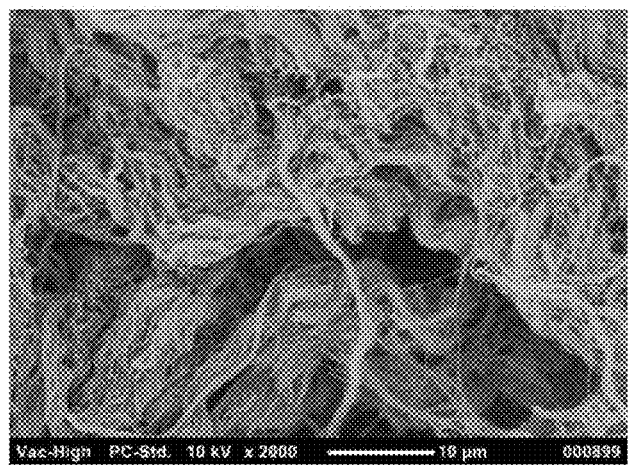
Figure 7C:
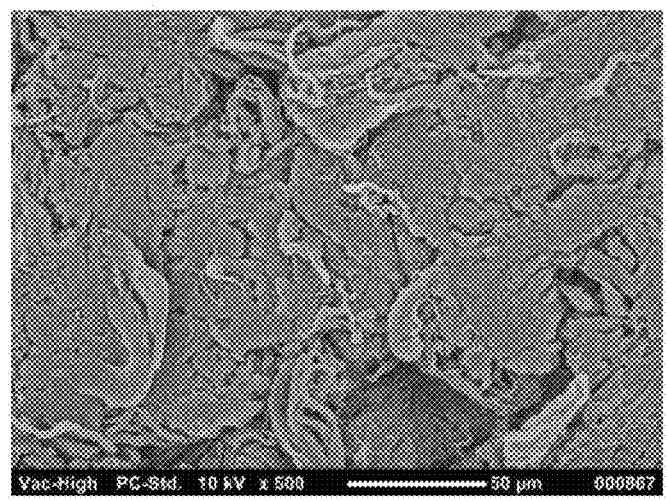
Figure 7D:
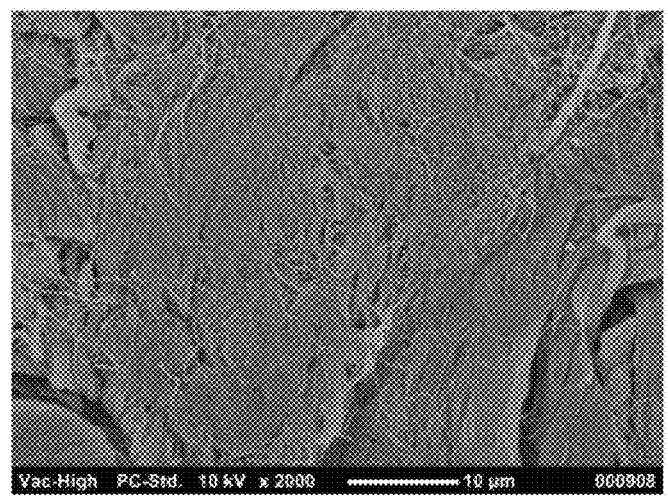

Electron Microscopy:

Rehydrated samples were fixed, dehydrated, and prepared in the manner described in Example 1 for SEM observation. FIGS. 7A-7D are scanning electron micrographs for a control acellular porcine dermal material (FIGS. 7A and 7B) and a shaped tissue product (FIGS. 7C and 7D). The low magnification images (FIGS. 7A and 7C) show that the treatment resulted in collagen fiber realignment. Further, the higher magnification images (FIGS. 7B and 7D) demonstrate that the processing brought collagen fibers closer to each others, but did not alter the collagen fiber structures.

Tissue Permeability:

A Franz-cell diffusion chamber with a 0.9 cm opening was used to measure the diffusion rate of fluorescein isothiocyanate (FITC)-labeled BSA across tissue matrix sheets. The concentration of FITC-BSA was maintained at 10 µg/ml at the donor chamber. The fluorescence of the solution in the receptor chamber was measured every hour for 7 hours. On completion of the diffusion assay, tissue samples were cryo-sectioned to 10-micron slices and imaged using a fluorescence-microscope.

Figure 8:
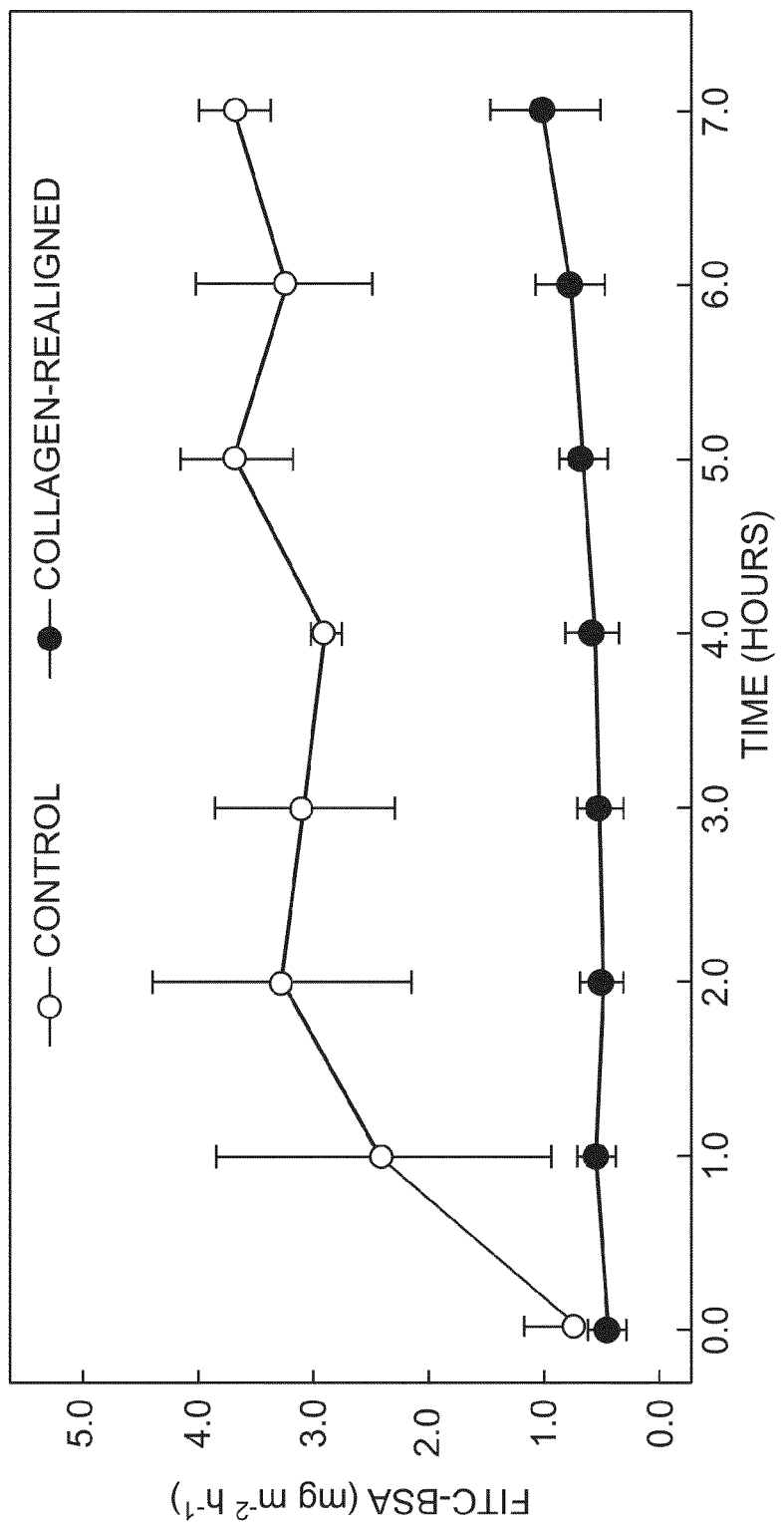
FIG. 8 is a plot of the diffusion rate of fluorescein isothiocyanate (FITC)-labeled borine serum albumin (BSA) across tissue matrix sheets in a Franz-cell diffusion chamber for an acellular porcine dermal material and a shaped tissue product produced according to certain embodiments.
Figure 9:
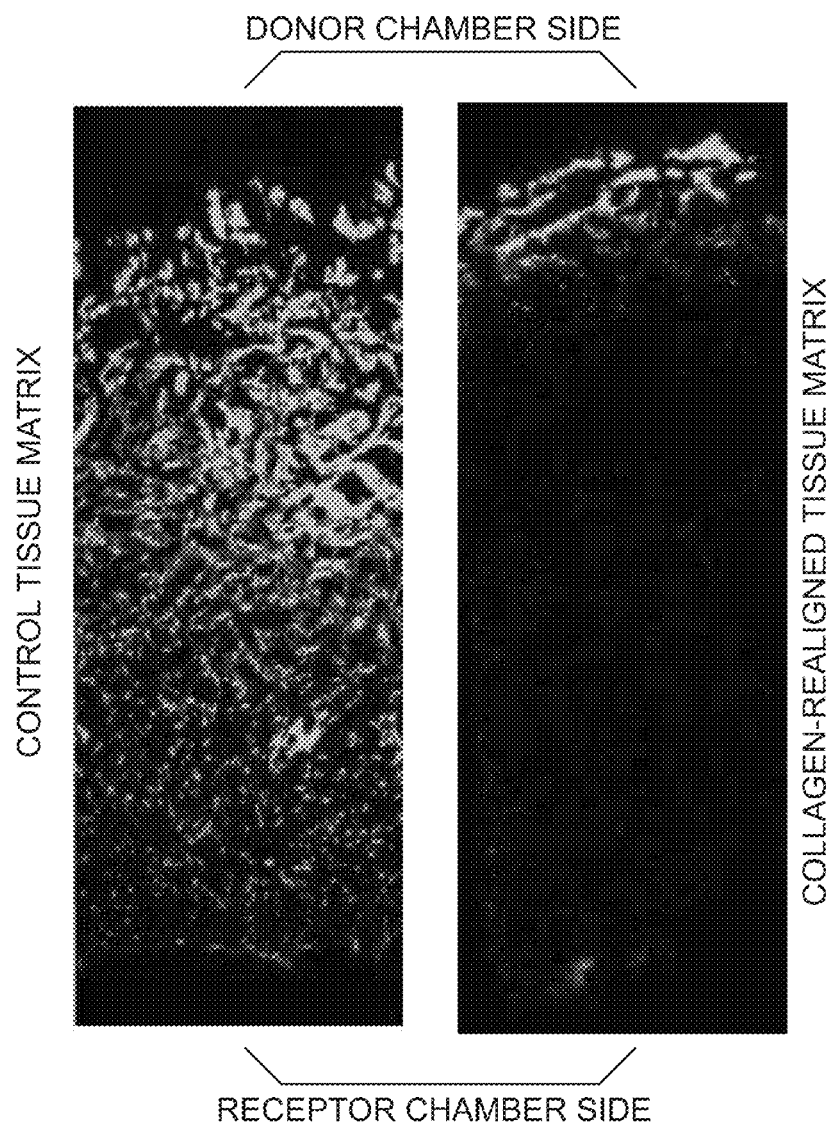
FIG. 9 includes fluorescence microscopy images of an acellular porcine dermal material and a shaped tissue product after exposure to fluorescein isothiocyanate (FITC)-labeled BSA in a Franz-cell diffusion chamber.

FIG. 8 is a plot of the diffusion rate of fluorescein isothiocyanate (FITC)-labeled BSA across tissue matrix sheets in a Franz-cell diffusion chamber for an acellular porcine dermal material and a shaped tissue product produced as described in this example. FIG. 9 includes fluorescence microscopy images of an acellular porcine dermal material and a shaped tissue product, respectively, after exposure to Fluorescein isothiocyanate (FITC)-labeled BSA in a Franz-cell diffusion chamber.

As shown, in the diffusion rate plot and microscopy images, the diffusion rate through the shaped tissue product was significantly less than the diffusion rate through the acellular porcine dermal matrix that had not been reshaped. This data demonstrates that the collagen realignment method can modify the permeability of a tissue matrix, and can reduce the permeability of tissue matrices.

Experiment #3

Shaping of Flat Acellular Porcine Dermal Sheets into 3D Shapes

Porcine skin was soaked in 0.2% calcium hydroxide solution for 5 days to loosen the epidermis and hair, and the epidermis and hair were mechanically removed by scraping. De-epidermized, de-haired dermis was neutralized with acetic acid and washed extensively in distilled water for 48 hours. Cleaned dermis was then de-cellularized by soaking in a solution containing 2% (w/v) sodium deoxycholate solution and 10 mM ETDA for 40 hours. After decellularization, the dermal matrix (~2 mm thick) was washed in PBS solution to remove residual detergent.

Figure 10:
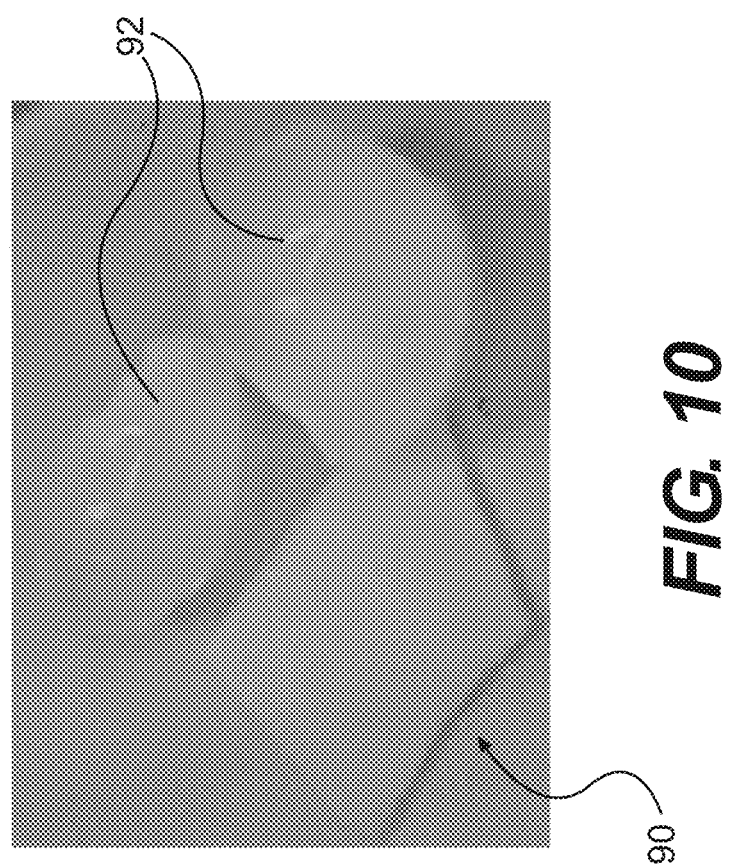
FIG. 10 is a photo of an acellular porcine dermal material and shaped tissue product produced according to certain embodiments.
Figure 11A:
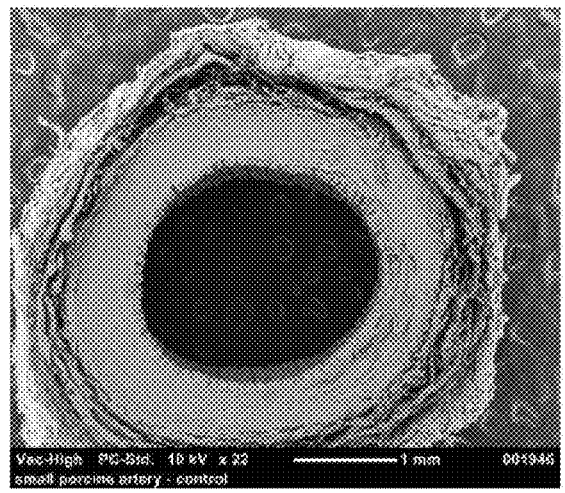
FIGS. 11A-11D are scanning electron micrographs for an acellular porcine artery and a shaped tissue product produced according to certain embodiments.
Figure 11B:
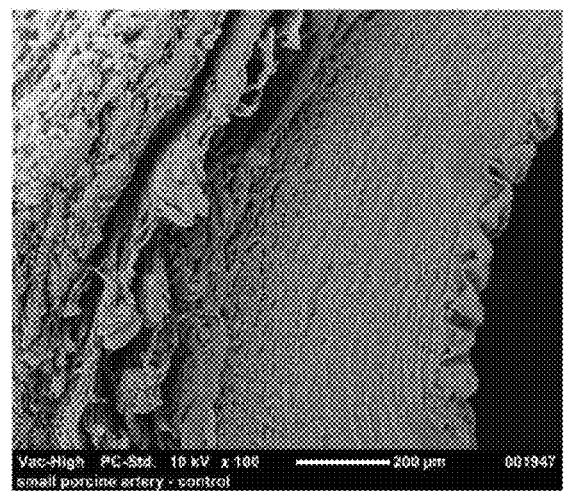
Figure 11C:
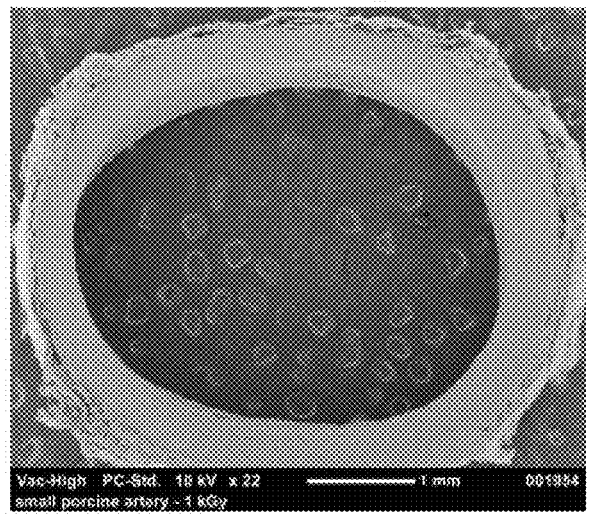
Figure 11D:
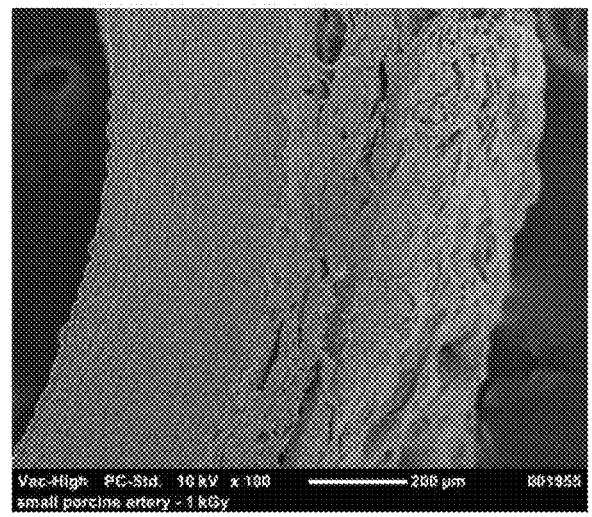

To shape the dermal sheet into a 3D curved tissue matrix, the sheet was partially dehydrated by blot drying with GAMMA WIPES®. The sheet was then mounted onto a mold having a semi-spherical shape under tension (~5 N). The sheet was secured in place with sutures. The mounted material was packaged in a foil-to-foil bag and irradiated with 16.7 kGy e-beam radiation. E-beam treated dermis was removed from the mold and fully rehydrated in PBS solution. An untreated sheet of acellular porcine dermis 90 and shaped tissue products 92 are shown in FIG. 10. As shown, the shaped tissue product maintained a stable three-dimensional cup shape, but remained flexible and had a feel that was very similar to the untreated acellular sheet.

Experiment #4

Shaping of Human Dermal Sheets into 3D Forms

Human skin was obtained from a cadaver donor. The epidermis was removed using a dermatome. The dermal tissue (~2.5 mm) was de-cellularized with 2% (w/v) sodium deoxycholate for 24 hours and was washed in PBS for 20 hours to remove detergent residues. A piece of decellularized dermal sheet was blot-dried and mounted onto a plastic cone (φ=4 cm). A second plastic cone was placed on top to secure the dermal matrix in the cone configuration. The construct was packaged in a foil-to-foil bag and irradiated by e-beam at a dose of 16.7 kGy.

E-beam treated dermis retained its cone shape after it was removed from the plastic molds (not shown). Other shapes were produced by folding dermal sheets to produce angled/folder configurations (results not shown).

Experiment #5

Reorientation of Collagen Fibers in Acellular Porcine Artery

Porcine carotid arteries (7 to 8 cm long) were dissected from animals' necks and were separated into two groups according to their outer diameter (Group A, 5 to 6 mm; Group B, 7 to 8 mm). Dissected arteries were rinsed for 30 min with 0.5% (w/v) TRITON X100 to remove blood. Arteries were frozen and thawed 3 times in 2% sodium deoxycholate solution containing an antibiotic cocktail (50 µg/ml penicillin, 1.25 µg/ml amphotercin B, and 50 µg/ml streptomycin). After the freeze-thaw cycles, arteries were de-cellularized at 37° C. for 96 hours in the same sodium deoxycholate solution. De-cellularized arteries were washed 4 times (2 hours for each wash) with Dulbecco's PBS with 50 u/ml penicillin, 1.25 µg/ml amphotercin B, and 50 µg/ml streptomycin. Half of the processed arteries from Group A and Group B were stored at 4° C. in PBS with the antibiotics. The other half of the processed arteries were subjected to gamma irradiation. A 5-mm surgical drain was inserted into each artery for support, and then the artery was blot-dried with GAMMA WIPES®. The blotting process was also used to applied mechanical pressure (compression) to the tissue matrix to cause reorientation of collagen fibers within the tissue matrix.

After blot-drying, arteries were packaged in sterile plastic film bags and secondary foil-to-foil bags. The arteries were irradiated with 1 kGy gamma radiation. The de-cellularization process removed endothelial cells from the intima, smooth muscle cells from the media, and fibroblast cells in the adventitia. The de-cellularized arteries comprised very loose collagen and elastin tissue matrices that could collapse on their own weight, while the shaped product (dehydrated and collagen realigned) maintained an open lumen with a tubular structure when laid on a flat surface.

FIGS. 11A-11D are scanning electron micrographs for an acellular porcine artery (FIGS. 11A and 11B) that had not be blot dried and irradiated, and for a shaped tissue product (FIGS. 11C and 11D) comprising an acellular artery that had been blot dried and irradiate. The partial dehydration and irradiation increased the strength of the arterial matrix, preventing the tubular structure from collapsing under its own weight. In addition, as can be seen in FIGS. 11A-11D, the treated arterial tissue matrices had more dense collagen fibers that were reoriented during blot drying.

Experiment #6

Stabilization of Rolled Human and Porcine Dermis Matrices

ALLODERM® and STRATTICE™ dermal tissue matrices were obtained from LifeCell Corporation. ALLODERM® is a freeze-dried acellular human dermal matrix, and STRATTICE™ is a hydrated acellular porcine dermal matrix. The ALLODERM® tissue matrices were aseptically rehydrated in PBS and washed three times to remove cryo-protectants. The rehydrated human dermal matrices were stored at 4° C. until ready to use. STRATTICE™ tissue matrices was aseptically washed in PBS three times to remove tissue preservation solutions.

After hydration, the human and porcine dermal tissue matrices were flexible sheets that could be rolled into a cylindrical shape. However, the rolled sheets would easily unfolded to flat sheets when placed into a saline solution. To stabilize the sheets rolls, human and porcine dermal sheets were blot-dried to a water content of about 75% (w/w) for ALLODERM® and 70% (w/w) for STRATTICE™. The blot-dried (partially dehydrated) sheets were rolled using surgical drain tubes. The rolled sheets were packaged in sterile plastic film bags and secondary foil-to-foil bags and were irradiated with 1 kGy gamma. After gamma irradiation, the rolled dermal matrices did not unfold when placed in saline solutions.

Figure 12B:
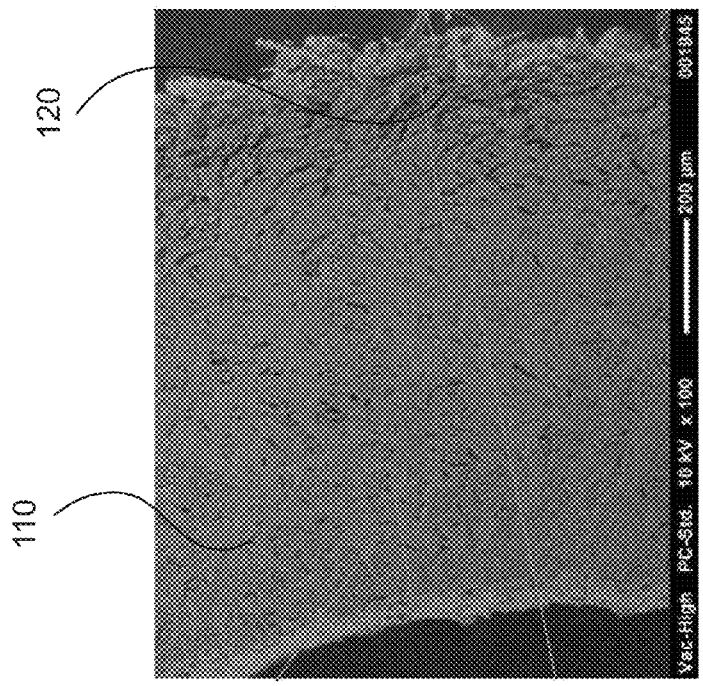
FIG. 12B is a scanning electron micrograph of a shaped tissue product produced according to certain embodiments.
Figure 12A:
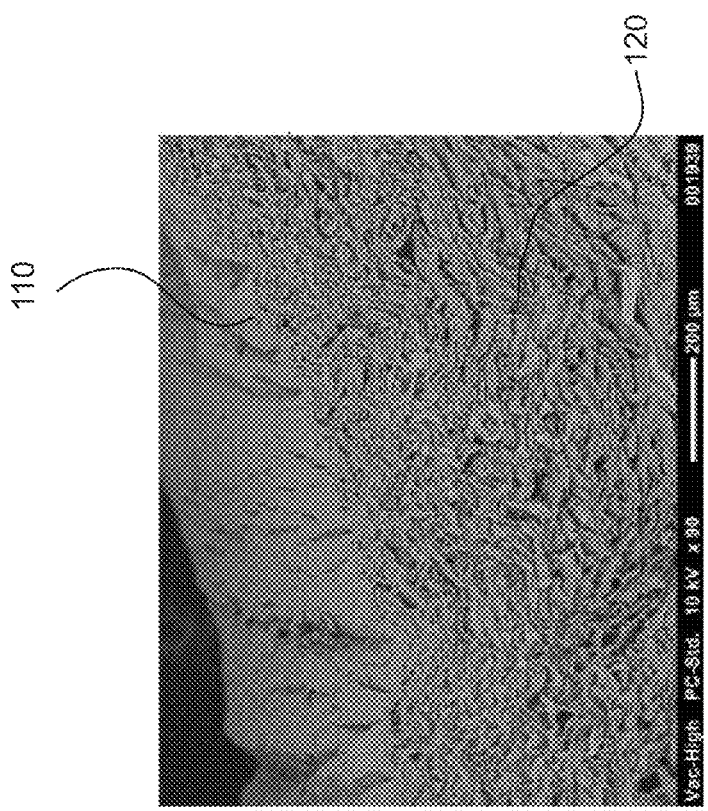
FIG. 12A is a scanning electron micrograph of a shaped tissue product produced according to certain embodiments.

The samples were prepared for SEM analysis, as described in example 1. FIGS. 12A and 12B are SEM images of shaped human dermal acellular tissue matrices and shaped porcine dermal acellular tissue matrices, respectively. As shown, the collagen fibers had areas of compression 110 and stretching 120 where the fibers were stably reoriented to form a tubular structure.

Acellular Tissue Matrices

The term "acellular tissue matrix," as used herein, refers generally to any tissue matrix that is substantially free of cells and/or cellular components. Skin, parts of skin (e.g., dermis), and other tissues such as blood vessels, heart valves, fascia, cartilage, bone, and nerve connective tissue may be used to create acellular matrices within the scope of the present disclosure. Acellular tissue matrices can be tested or evaluated to determine if they are substantially free of cell and/or cellular components in a number of ways. For example, processed tissues can be inspected with light microscopy to determine if cells (live or dead) and/or cellular components remain. In addition, certain assays can be used to identify the presence of cells or cellular components. For example, DNA or other nucleic acid assays can be used to quantify remaining nuclear materials within the tissue matrices. Generally, the absence of remaining DNA or other nucleic acids will be indicative of complete decellularization (i.e., removal of cells and/or cellular components). Finally, other assays that identify cell-specific components (e.g., surface antigens) can be used to determine if the tissue matrices are acellular.

In general, the steps involved in the production of an acellular tissue matrix include harvesting the tissue from a donor (e.g., a human cadaver or animal source) and cell removal under conditions that preserve biological and structural function. In certain embodiments, the process includes chemical treatment to stabilize the tissue and avoid biochemical and structural degradation together with or before cell removal. In various embodiments, the stabilizing solution arrests and prevents osmotic, hypoxic, autolytic, and proteolytic degradation, protects against microbial contamination, and reduces mechanical damage that can occur with tissues that contain, for example, smooth muscle components (e.g., blood vessels). The stabilizing solution may contain an appropriate buffer, one or more antioxidants, one or more oncotic agents, one or more antibiotics, one or more protease inhibitors, and/or one or more smooth muscle relaxants.

The tissue is then placed in a decellularization solution to remove viable cells (e.g., epithelial cells, endothelial cells, smooth muscle cells, and fibroblasts) from the structural matrix without damaging the biological and structural integrity of the collagen matrix. The decellularization solution may contain an appropriate buffer, salt, an antibiotic, one or more detergents (e.g., TRITON X-100™, sodium deoxycholate, polyoxyethylene (20) sorbitan mono-oleate), one or more agents to prevent cross-linking, one or more protease inhibitors, and/or one or more enzymes. In some embodiments, the decellularization solution comprises 1% TRITON X-100™ in RPMI media with Gentamicin and 25 mM EDTA (ethylenediaminetetraacetic acid). In some embodiments, the tissue is incubated in the decellularization solution overnight at 37° C. with gentle shaking at 90 rpm. In certain embodiments, additional detergents may be used to remove fat from the tissue sample. For example, in some embodiments, 2% sodium deoxycholate is added to the decellularization solution.

After the decellularization process, the tissue sample is washed thoroughly with saline. In some exemplary embodiments, e.g., when xenogenic material is used, the decellularized tissue is then treated overnight at room temperature with a deoxyribonuclease (DNase) solution. In some embodiments, the tissue sample is treated with a DNase solution prepared in DNase buffer (20 mM HEPES (4-(2-hydroxyethyl)-1-piperazineethanesulfonic acid), 20 mM $CaCl_2$ and 20 mM $MgCl_2$). Optionally, an antibiotic solution (e.g., Gentamicin) may be added to the DNase solution. Any suitable buffer can be used as long as the buffer provides suitable DNase activity.

While an acellular tissue matrix may be made from one or more individuals of the same species as the recipient of the acellular tissue matrix graft, this is not necessarily the case. Thus, for example, an acellular tissue matrix may be made from porcine tissue and implanted in a human patient. Species that can serve as recipients of acellular tissue matrix and donors of tissues or organs for the production of the acellular tissue matrix include, without limitation, mammals, such as humans, nonhuman primates (e.g., monkeys, baboons, or chimpanzees), pigs, cows, horses, goats, sheep, dogs, cats, rabbits, guinea pigs, gerbils, hamsters, rats, or mice.

Elimination of the α-gal epitopes from the collagen-containing material may diminish the immune response against the collagen-containing material. The α-gal epitope is expressed in non-primate mammals and in New World monkeys (monkeys of South America) as well as on macromolecules such as proteoglycans of the extracellular components. U. Galili et al., J. Biol. Chem. 263: 17755 (1988). This epitope is absent in Old World primates (monkeys of Asia and Africa and apes) and humans, however. Id. Anti-gal antibodies are produced in humans and primates as a result of an immune response to α-gal epitope carbohydrate structures on gastrointestinal bacteria. U. Galili et al., Infect. Immun. 56: 1730 (1988); R. M. Hamadeh et al., J. Clin. Invest. 89: 1223 (1992).

Since non-primate mammals (e.g., pigs) produce α-gal epitopes, xenotransplantation of collagen-containing material from these mammals into primates often results in rejection because of primate anti-Gal binding to these epitopes on the collagen-containing material. The binding results in the destruction of the collagen-containing material by complement fixation and by antibody dependent cell cytotoxicity. U. Galili et al., Immunology Today 14: 480 (1993); M. Sandrin et al., Proc. Natl. Acad. Sci. USA 90: 11391 (1993); H. Good et al., Transplant. Proc. 24: 559 (1992); B. H. Collins et al., J. Immunol. 154: 5500 (1995). Furthermore, xenotransplantation results in major activation of the immune system to produce increased amounts of high affinity anti-gal antibodies. Accordingly, in some embodiments, when animals that produce α-gal epitopes are used as the tissue source, the substantial elimination of α-gal epitopes from cells and from extracellular components of the collagen-containing material, and the prevention of re-expression of cellular α-gal epitopes can diminish the immune response against the collagen-containing material associated with anti-gal antibody binding to α-gal epitopes.

To remove α-gal epitopes, after washing the tissue thoroughly with saline to remove the DNase solution, the tissue sample may be subjected to one or more enzymatic treatments to remove certain immunogenic antigens, if present in the sample. In some embodiments, the tissue sample may be treated with an α-galactosidase enzyme to eliminate α-gal epitopes if present in the tissue. In some embodiments, the tissue sample is treated with α-galactosidase at a concentration of 300 U/L prepared in 100 mM phosphate buffer at pH 6.0. In other embodiments, the concentration of α-galactosidase is increased to 400 U/L for adequate removal of the α-gal epitopes from the harvested tissue. Any suitable enzyme concentration and buffer can be used as long as sufficient removal of antigens is achieved.

Alternatively, rather than treating the tissue with enzymes, animals that have been genetically modified to lack one or more antigenic epitopes may be selected as the tissue source. For example, animals (e.g., pigs) that have been genetically engineered to lack the terminal α-galactose moiety can be selected as the tissue source. For descriptions of appropriate animals see co-pending U.S. application Ser. No. 10/896,594 and U.S. Pat. No. 6,166,288, the disclosures of which are incorporated herein by reference in their entirety. In addition, certain exemplary methods of processing tissues to produce acellular matrices with or without reduced amounts of or lacking alpha-1,3-galactose moieties, are described in Xu, Hui. et al., "A Porcine-Derived Acellular Dermal Scaffold that Supports Soft Tissue Regeneration: Removal of Terminal Galactose-α-(1,3)-Galactose and Retention of Matrix Structure," Tissue Engineering, Vol. 15, 1-13 (2009), which is incorporated by reference in its entirety.

After the acellular tissue matrix is formed, histocompatible, viable cells may optionally be seeded in the acellular tissue matrix to produce a graft that may be further remodeled by the host. In some embodiments, histocompatible viable cells may be added to the matrices by standard in vitro cell co-culturing techniques prior to transplantation, or by in vivo repopulation following transplantation. In vivo repopulation can be by the recipient's own cells migrating into the acellular tissue matrix or by infusing or injecting cells obtained from the recipient or histocompatible cells from another donor into the acellular tissue matrix in situ. Various cell types can be used, including embryonic stem cells, adult stem cells (e.g. mesenchymal stem cells), and/or neuronal cells. In various embodiments, the cells can be directly applied to the inner portion of the acellular tissue matrix just before or after implantation. In certain embodiments, the cells can be placed within the acellular tissue matrix to be implanted, and cultured prior to implantation.

What is claimed is:

1. A method for shaping a tissue matrix, comprising:
   selecting a collagen-containing tissue matrix;
   partially dehydrating the tissue matrix;
   applying mechanical forces to the tissue matrix to change the orientation of collagen fibers within the tissue matrix; and
   exposing the tissue matrix while partially dehydrated to ionizing radiation to cross-link at least a portion of the tissue matrix.

2. The method of claim 1, wherein the tissue matrix is an a cellular tissue matrix.

3. The method of claim 1, wherein the tissue matrix comprises a dermal tissue matrix.

4. The method of claim 1, wherein the tissue is selected from fascia, pericardial tissue, dura, umbilical cord tissue, placental tissue, cardiac valve tissue, ligament tissue, tendon tissue, arterial tissue, venous tissue, neural connective tissue, urinary bladder tissue, ureter tissue, and intestinal tissue.

5. The method of claim 1, wherein partially dehydrating the tissue matrix includes removing water to produce a tissue matrix containing between 95% (w/w) and 50% (w/w) water content.

6. The method of claim 5, wherein the water content is between 80% (w/w) and 65% (w/w).

7. The method of claim 1, further comprising rehydrating the tissue matrix.

8. The method of claim 1, wherein the radiation is applied at a dose between 5 Gy and 50 kGy.

9. The method of claim 1, wherein the radiation is applied at a dose between 5 Gy and 20 kGy.

10. The method of claim 1, wherein the radiation is applied at a dose of less than 10 kGy.

11. The method of claim 1, wherein the radiation is applied at a dose of less than 5 kGy.

12. The method of claim 1, wherein the radiation is applied at a dose of less than 1 kGy.

13. The method of claim 1, wherein the radiation is selected from gamma radiation, e-beam radiation, and X-ray radiation.

14. The method of claim 1 or 2, wherein selecting a tissue matrix includes selecting a tissue matrix in the form of a flexible sheet.

\* \* \* \* \*